(12) United States Patent
Miki et al.

(10) Patent No.: US 8,058,303 B2
(45) Date of Patent: Nov. 15, 2011

(54) PHARMACEUTICAL COMPOSITION FOR EXTERNAL USE

(75) Inventors: Toyohiko Miki, Yokohama (JP); Hiroyuki Fujii, Yokohama (JP); Akira Nozawa, Yokohama (JP); Hirokazu Kobayashi, Yokohama (JP)

(73) Assignees: Nihon Nohyaku Co, Ltd, Chuo-ku, Tokyo (JP); Pola Pharma Inc, Sinagawa-ku, Tokyo (JP)

( * ) Notice: Subject to any disclaimer, the term of this patent is extended or adjusted under 35 U.S.C. 154(b) by 0 days.

(21) Appl. No.: 12/281,973

(22) PCT Filed: Oct. 2, 2006

(86) PCT No.: PCT/JP2006/319711
§ 371 (c)(1),
(2), (4) Date: Sep. 5, 2008

(87) PCT Pub. No.: WO2007/102243
PCT Pub. Date: Sep. 13, 2007

(65) Prior Publication Data
US 2009/0076109 A1 Mar. 19, 2009

(30) Foreign Application Priority Data

Mar. 8, 2006 (JP) .................................. 2006-062080
Aug. 8, 2006 (JP) .................................. 2006-215864

(51) Int. Cl.
*A61K 31/4178* (2006.01)
(52) U.S. Cl. ........................................................ 514/397
(58) Field of Classification Search ........................ None
See application file for complete search history.

(56) References Cited

U.S. PATENT DOCUMENTS

| | | | |
|---|---|---|---|
| 4,764,381 A | 8/1988 | Bodor et al. | |
| 5,753,256 A * | 5/1998 | Cordes et al. | 424/443 |
| 5,993,787 A | 11/1999 | Sun et al. | |
| 6,017,920 A | 1/2000 | Kamishita et al. | |
| 6,083,518 A | 7/2000 | Lindahl | |
| 6,428,654 B1 | 8/2002 | Cronan, Jr. et al. | |
| 6,585,963 B1 | 7/2003 | Quan et al. | |
| 6,740,326 B1 | 5/2004 | Meyer et al. | |
| 2003/0235541 A1* | 12/2003 | Maibach et al. | 424/61 |
| 2004/0208906 A1 | 10/2004 | Tatara et al. | |
| 2005/0232879 A1 | 10/2005 | Sasagawa et al. | |
| 2006/0140984 A1 | 6/2006 | Tamarkin et al. | |
| 2008/0031835 A1 | 2/2008 | Kawamura et al. | |
| 2009/0030059 A1 | 1/2009 | Miki et al. | |
| 2009/0076109 A1 | 3/2009 | Miki et al. | |
| 2009/0137651 A1 | 5/2009 | Kobayashi et al. | |
| 2009/0202602 A1* | 8/2009 | Ishima et al. | 424/405 |
| 2010/0168200 A1 | 7/2010 | Masuda et al. | |
| 2010/0173965 A1 | 7/2010 | Masuda et al. | |
| 2010/0204293 A1 | 8/2010 | Masuda et al. | |

FOREIGN PATENT DOCUMENTS

| | | |
|---|---|---|
| EP | 1 138 314 | 10/2001 |
| EP | 1 522 316 | 4/2005 |
| EP | 1 537 868 | 6/2005 |
| JP | 62-093227 | 4/1987 |
| JP | 01-242525 | 9/1989 |
| JP | 01-246219 | 10/1989 |
| JP | 02-264723 | 10/1990 |
| JP | 02-275877 | 11/1990 |
| JP | 05-306223 | 11/1993 |
| JP | 06-199701 | 7/1994 |
| JP | 06-211651 | 8/1994 |
| JP | 07-206711 | 8/1995 |
| JP | 07-223971 | 8/1995 |
| JP | 08-020527 | 1/1996 |
| JP | 10-152433 | 6/1998 |
| JP | 10-226639 | 8/1998 |
| JP | 10-226686 | 8/1998 |
| JP | 2001-064206 | 3/2001 |
| JP | 2002-114680 | 4/2002 |
| JP | 2002-193755 | 7/2002 |
| JP | 2002-363070 | 12/2002 |
| JP | 2003-252798 | 9/2003 |
| JP | 2004-529923 | 9/2004 |
| JP | 2005-154306 | 6/2005 |
| JP | 2005-289879 | 10/2005 |
| RU | 2 270 894 C2 | 3/2004 |
| WO | WO 95/30440 | 11/1995 |
| WO | WO 96/11710 | 4/1996 |
| WO | WO 96/40047 | 12/1996 |
| WO | WO 97/02821 | 1/1997 |

(Continued)

OTHER PUBLICATIONS

Niwano, et al. "Efficacy of NND-502, a Novel Imidazole Antimycotic Agent, in Experimental Models of *Candida albicans* and *Aspergillus fumigatus* Infections," *International Journal of Antimicrobial Agents*, vol. 12, pp. 221-228, 1999.

Uchida, et al. "In vitro Antifungal Activity of Luliconazole (NND-502), a Novel Imidazole Antifungal Agent," *J. Infect Chemother.*, vol. 10, pp. 216-219, 2004.

Uchida, et al. "In vitro Activity of Novel Imidazole Antifungal Agent NND-502 Against *Malassezia* species," *International Journal of Antimicrobial Agents*, vol. 21, pp. 234-238, 2003.

Borrás-Blasco, et al. "A Mathematical Approach to Predicting the Percutaneous Absorption Enhancing Effect of Sodium Lauryl Sulphate," *International Journal of Pharmaceutics*, vol. 269, pp. 121-129, 2004.

(Continued)

*Primary Examiner* — Phyllis G. Spivack
(74) *Attorney, Agent, or Firm* — Knobbe, Martens, Olson & Bear, LLP

(57) ABSTRACT

Provided is a pharmaceutical composition for external use which includes the following components: 1) luliconazole and/or a salt thereof; 2) N-methyl-2-pyrollidone; and 3) benzyl alcohol and/or diester of a dibasic acid. The diester of the dibasic acid is a diethyl ester or a diisopropyl ester of a dibasic acid having 6-10 carbon atoms. The pharmaceutical composition is useful for the treatment of a mycotic disease such as foot trichophytosis, trichophytosis corporis, trichophytosis on a hard keratin or hyperkeratotic portion, onychomycosis, particularly on a nail, or dermatomycosis.

15 Claims, No Drawings

FOREIGN PATENT DOCUMENTS

| | | |
|---|---|---|
| WO | WO 00/01384 | 1/2000 |
| WO | WO 02/062336 | 8/2002 |
| WO | WO 02/083084 | 10/2002 |
| WO | WO 02/087570 | 11/2002 |
| WO | WO 03/020248 | 3/2003 |
| WO | WO 03/105841 | 12/2003 |
| WO | WO 2004/021968 | 3/2004 |
| WO | WO 2004/084826 | 10/2004 |
| WO | WO 2005/099764 | 10/2005 |
| WO | WO 2005/123136 | 12/2005 |
| WO | WO 2006/038317 | 4/2006 |
| WO | WO 2007/077806 | 7/2007 |
| WO | WO 2007077806 * | 7/2007 |
| WO | WO 2007/102242 | 9/2007 |
| WO | WO 2007/077806 * | 12/2007 |

OTHER PUBLICATIONS

Martins, et al. "In vitro Sensitivity of Dermatophytes to Urea," *Clinics*, vol. 61, No. 1, pp. 9-14, 2006.

Uchida, et al. "In vitro Antifungal Activity of Luliconazole (NND-502), a Novel Imidazole Antifungal Agent," *Journal of Infectious Chemotherapy*, vol. 10, pp. 216-219, 2004.

Article, "Treatment" in 2 pages downloaded from http://www.babymd,net/dryskin.htm date unknown, 2011.

Niwano, et al. "In Vitro and In Vivo Antidermatophyte Activities of NND-4502, a Novel Optically Active Imidazole Antimycotic Agent," *Antimicrobial Agents and Chemotherapy*, vol. 42, No. 4, pp. 967-970, Apr. 1998.

* cited by examiner

PHARMACEUTICAL COMPOSITION FOR EXTERNAL USE

CROSS-REFERENCE TO RELATED APPLICATIONS

This application is the U.S. National Phase under 35 U.S.C. §371 of International Application PCT/JP2006/319711, filed Oct. 2, 2006, which was published in a non-English language, which claims priority to JP Patent Application No. 2006-062080, filed Mar. 8, 2006 and JP Patent Application No. 2006-215864, filed Aug. 8, 2006.

TECHNICAL FIELD

The present invention relates to a pharmaceutical composition for external use, and more particularly, to a pharmaceutical composition for external use for treatment or prevention of onychomycosis or hyperkeratotic trichophytosis.

BACKGROUND ART

The Japanese archipelago extends from a subtropical zone to a temperate zone and has a warm climate high in humidity, which is liable to facilitate propagation of fungi such as molds. In addition, due to westernization of clothes, people are now accustomed to wearing shoes on feet. Accordingly, afoot serves as a favorable environment for the propagation of the fungi, leading to mycotic skin diseases that are serious social issues nowadays. Of those, onychomycosis has a low complete cure rate and high relapsing and reinfection rates. Therefore, an effective therapy has been demanded.

Conventionally, treatments mainly using tolnaftate formulations have been conducted on such diseases. In recent years, imidazole-based antifungal agents, such as bifonazole and itraconazole, are mainly used.

As the imidazole-based antifungal agents, there are commercially available imidazole-based antifungal agents such as those represented by the general formula (1) described below, specifically, luliconazole represented by the structural formula (1) below and lanoconazole represented by the structural formula (2) below. The above-mentioned luliconazole is currently the newest imidazole-based antifungal agent, and a commercially available product called "Lulicon" (registered trademark) is also present (e.g., see Patent Document 1 and Patent Document 2).

The compounds each represented by the general formula (1) have a wide antifungal spectrum, in particular, remarkable antifungal activity against dermatophytes. In addition, the compounds are also characterized by their extremely high retention in the stratum corneum and thus expected to be applied to the treatment of onychomycosis.

However, even though the agents show high antifungal effects and high retention in the stratum corneum and they excel in actual scenes of therapeutic experiments, the effects of the agents have not reached a level expected from the results of in vitro studies.

This fact may be caused by the presence of a physico-chemical factor that prevents any of those agents from reaching to a focus and effecting thereon. In other words, it is implicated that, by overcoming such an inhibitory factor by pharmaceutical countermeasures, those agents may satisfactory exert their inherent antifungal effects, thereby providing more excellent antifungal pharmaceutical compositions. As information that confirms such an implication, there is reported that, for example, crystal precipitation of lanoconazole in formulation thereof is an inhibitory effect on the penetration of the agent into the body (see, for example, Patent Document 3). In this document, even though the crystal precipitation of lanoconazole is prevented by the addition of lactic acid, the use of such an inhibitory procedure does not sufficiently prevent the crystal precipitation at the present. The causes of such crystal precipitation include: (1) the solubility of a compound represented by the general formula (1) below and/or a salt thereof to formulation components; (2) when a formulation is applied to the skin or nail, the interaction between the formulation and the surface structure of the skin or nail or the interaction between the formulation and any component such as a salt on the surface of the skin or nail; (3) the influence of vaporization or the like of a solvent; and so on, but most parts of mechanisms thereof are unknown.

The above-mentioned causes, by which expected results cannot be obtained, are thought to be phenomena specific to the compound represented by the general formula (1) and/or a salt thereof. Therefore, it is implicated that another inhibitory factor for the expression of a pharmaceutical effect is a barrier function of stratum corneum, which tends to prevent the compound from passing through the stratum corneum and reaching to a focus. In addition, it is further implicated that any of those compounds is allowed to be easily transferred into the blood after passing through the stratum corneum and the accumulation of the agent on the focus is thus inhibited, so the compound is prevented from exerting its effect. In other words, the factors that inhibit the expression of effects are complicated, so such a problem cannot be sufficiently solved at the present.

On the other hand, N-methyl-2-pyrrolidone has been known as a component capable of increasing the penetrability of an antifungal agent to stratum corneum and also considered to be used in combination with lanoconazole (see, for example Patent Document 4).

However, a formulation, in which a compound represented by the general formula (1) below and/or a salt thereof including lanoconazole is used in combination with N-methyl-2-pyrrolidone, has not been known at all. In addition, in such a formulation, the compound represented by the general formula (1) below has not been known to satisfactory exert its inherent effect at all.

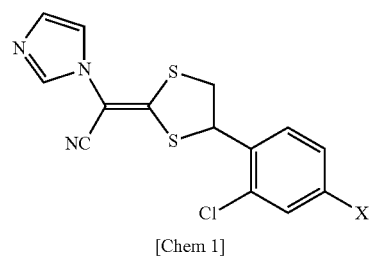

General formula (1)

[Chem 1]

(where X represents a hydrogen atom or a chlorine atom)

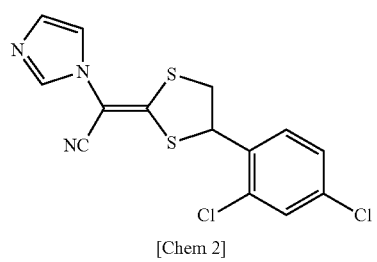

Structural formula (1)

[Chem 2]

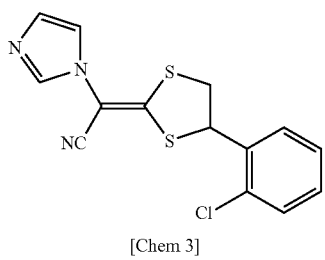

Structural formula (2)

[Chem 3]

Patent Document 1: JP 62-93227 A
Patent Document 2: JP 10-226686 A
Patent Document 3: JP 2002-363070 A
Patent Document 4: JP 2004-529923 A

DISCLOSURE OF THE INVENTION

Problem to be Solved by the Invention

The present invent has been made under such circumstances, and an object of the present invention is to provide a pharmaceutical composition for external use containing a compound represented by the general formula (1) described above and/or a salt thereof and having an excellent antifungal effect by developing means for preventing an inhibitory factor from inhibiting the expression of an effect of the composition.

Means for Solving the Problem

In consideration of such circumstances, the inventors of the present invention have made intensive studies and efforts to obtain means for preventing the factor which prohibit the antifungal efficacy of the pharmaceutical composition for external use, which contains a compound represented by the general formula (1) described above and/or a salt thereof, and finally completed the present invention by finding that such an undesirable factor can be deprived by coexistence with N-methyl-2-pyrrolidone.

That is, the present invention is described below:

(1) A pharmaceutical composition for external use, including:
i) a compound represented by the general formula (1) below and/or a salt thereof; and
ii) N-methyl-2-pyrrolidone:

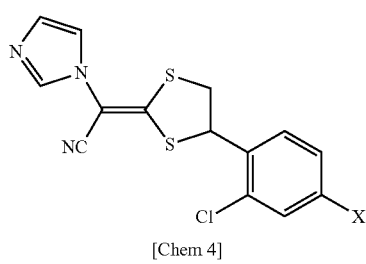

General formula (1)

[Chem 4]

where, X represents a hydrogen atom or a chlorine atom.

(2) A pharmaceutical composition for external use according to claim 1, in which the compound represented by the general formula (1) is luliconazole or lanoconazole.

(3) A pharmaceutical composition for external use according to the above-mentioned item (1) or (2), further including benzyl alcohol.

(4) A pharmaceutical composition for external use according to the above-mentioned item (1), further including a diester of a dibasic acid.

(5) A pharmaceutical composition for external use according to the above-mentioned item (4), in which the diester of the dibasic acid is a diester of a dibasic acid and an alcohol having 1 to 4 carbon atoms.

(6) A pharmaceutical composition for external use according to the above-mentioned item (4), in which the diester of the dibasic acid is a diethyl ester or a diisopropyl ester of adipic acid or sebacic acid.

(7) A pharmaceutical composition for external use according to the above-mentioned item (1), further including an α-hydroxycarboxylic acid and/or a salt thereof.

(8) A pharmaceutical composition for external use according to the above-mentioned item (7), in which the α-hydroxycarboxylic acid is lactic acid.

(9) A pharmaceutical composition for external use according to the above-mentioned item (1), which is provided for treatment or prevention of onychomycosis.

(10) A pharmaceutical composition for external use according to the above-mentioned item (1), which is provided for treatment or prevention of hyperkeratotic trichophytosis.

Effects of the Invention

According to the present invention, there can be provided a pharmaceutical composition for external use, which contains a compound represented by the general formula (1) described above and/or a salt thereof and has an excellent antifungal effect by developing means for preventing an inhibitory factor from inhibiting the expression of an effect of the composition.

BEST MODE FOR CARRYING OUT THE INVENTION (1) Compound represented by general formula (1) and/or salt thereof (hereinafter, also referred to as compound or the like represented by the general formula (1)), which is essential component of pharmaceutical composition for external use according to the present invention (hereinafter, also referred to as the pharmaceutical composition of the present invention)

The pharmaceutical composition of the present invention contains any of compounds or the like represented by the general formula (1) as an essential component.

Preferred examples of the compounds represented by the general formula (1) include:
(R)-(−)-(E)-[4-(2,4-dichlorophenyl)-1,3-dithiolane-2-ylidene]-1-imidazolylacetonitrile (luliconazole), (R)-(+)-(E)-[4-(2-chlorophenyl)-1,3-dithiolane-2-ylidene]-1-imidazolyl acetonitrile, and
(E)-[4-(2-chlorophenyl)-1,3-dithiolane-2-ylidene]-1-imidazolyl acetonitrile (lanoconazole). Those compounds are known in the art and their manufacturing processes and antifungal properties are already known (see, for example, JP 62-93227 A (Patent Document 1 described above)). Of those, lanoconazole is preferable because it exerts a significant effect of the present invention.

In addition, "salt thereof" is not specifically limited as far as it is physiologically acceptable. Preferable examples thereof include: mineral acid salts such as hydrochloride, nitrate, sulfate, and phosphate; organic acid salts such as citrate, oxalate, lactate, and acetate; and sulfuric acid-containing salts such as mesilate and tosilate. In terms of safety and solubility, hydrochloride is more preferable.

One kind of the compounds or the like each represented by the general formula (1) can be used, or two or more kinds thereof can be used in combination. In the pharmaceutical composition of the present invention, the content of the compound or the like represented by the general formula (1) is preferably 0.1 to 30% by mass, more preferably 0.5 to 15% by mass in total with respect to the total amount of the pharmaceutical composition. The content of the compound or the like represented by the general formula (1) can be determined based on its solubility and formulation characteristics.

(2) N-methyl-2-pyrrolidone, essential component of pharmaceutical composition for external use according to the present invention The characteristic feature of the pharmaceutical composition for external use according to the present invention is to contain N-methyl-2-pyrrolidone as an essential component. N-methyl-2-pyrrolidone itself has been already used as one of additives for pharmaceutical compositions and there is a commercial product thereof, so that it can be available without difficulty. Such a component raises the dissolution stability of a formulation system of the compound or the like represented by the general formula (1) and prevents the precipitation of a crystal or insolublilized product to occur on an applied surface after 20 to 40 seconds from the application, which may be due to the interaction of the compound or the like with the surface structure of the skin or nail or with a substance present on the surface thereof. In addition, secondary effects may include suppression of an inhibitory factor for the penetrability of stratum corneum and an inhibitory factor for retention in a focus. For exerting the effects, the content of N-methyl-2-pyrrolidone is preferably 1 to 15% by mass, particularly preferably 3 to 10% by mass with respect to the total amount of the pharmaceutical composition. This component also has an effect of preventing a solution of an optically-active compound among the compounds represented by the above general formula (1) and/or a salt thereof from isomerization in a state of preservation.

(3) Benzyl alcohol used in a pharmaceutical composition for external use according to the present invention The pharmaceutical composition for external use according to the present invention may preferably contain benzyl alcohol. This component has been already used as one of additives for pharmaceutical compositions and there is a commercial product thereof, so that it can be available without difficulty. This component exerts an effect of preventing, in the presence of the above-mentioned N-methyl-2-pyrrolidone, a crystal or insolubilized product of the compound or the like represented by the above general formula (1) from precipitation on the living body when the compound or the like is applied thereto, and inhibition of penetration into the tissue of the living body, particularly penetration into the nail. For exerting the effects, the content of the component is preferably 1 to 15% by mass, particularly preferably 3 to 10% by mass with respect to the total amount of the pharmaceutical composition. In other words, if the content of the component is out of the above-mentioned range, the compound of the general formula (1) and/or the salt thereof may be precipitated as a crystal or insolubilized product when applied. In this way, by preventing the crystal precipitation, which occurs at the time of application, benzyl alcohol satisfactory exerts its inherent effect of penetrating through tissues.

(4) Diester of a dibasic acid used in pharmaceutical composition for external use according to the present invention The pharmaceutical composition for external use according to the present invention preferably contains a diester of a dibasic acid, in particular, any of the diesters of the dibasic acids and alcohols each having 1 to 4 carbon atoms. Examples of the dibasic acids include those having 1 to 10 carbon atoms, preferably, adipic acid, sebacic acid, oxalic acid, and carbonic acid. On the other hand, preferable examples of the alcohols each having 1 to 4 carbon atoms include methyl alcohol, ethyl alcohol, propyl alcohol, isopropyl alcohol, butyl alcohol, isobutyl alcohol, and tert-butyl alcohol.

Specific examples of the above diester of a dibasic acid preferably include diethyl adipate, diisopropyl adipate, diethyl sebacate, and diisopropyl sebacate with diisopropyl adipate and diethylsebacate being particulary preferable. The pharmaceutical composition for external use of the present invention may contain only one of those components or may contain two or more of them in combination. In the presence of the above N-methyl-2-pyrrolidone, the above component exerts an effect of preventing the factors that inhibit the penetration or retention of the compound represented by the above general formula (1) in a tissue, particularly in a growing portion of the stratum corneum and the nail, together with α-hydroxy acid and/or a salt thereof, or the like as described below. For exerting the effect, the content of the component is preferably 1 to 30% by mass, more preferably 5 to 15% by mass in total with respect to the total amount of the pharmaceutical composition.

(5) α-hydroxycarboxylic acid and/or a salt thereof used in pharmaceutical composition for external use according to the present invention The pharmaceutical composition for external use according to the present invention preferably contains an α-hydroxycarboxylic acid and/or a salt thereof (hereinafter, also referred to as "α-hydroxycarboxylic acid or the like").

Examples of the above α-hydroxycarboxylic acid include α-hydroxycarboxylic acids each having 2 to 5 carbon atoms. Of those, lactic acid, glycolic acid, malic acid, and so on can be preferably exemplified, and of those lactic acid is particularly preferable. Further, the salts thereof described above are not specifically limited as far as they are used in formulations and physiologically acceptable. Examples thereof preferably include: alkali metal salts such as sodium salt and potassium salt; alkaline earth metal salts such as calcium salt and magnesium salt; organic amine salts such as ammonium salt, triethylamine salt, and triethanol amine salt; and basic amino acid salt such as arginine salt and lysin salt. The pharmaceutical composition for external use of the present invention may contain only one of those components or may contain two or more of them in combination. In the pharmaceutical composition for external use of the present invention, the component has an effect of preventing the compound or the like represented by the above general formula (1), when applied, from formation and precipitation of a crystal on an applied surface. Such an inhibitory effect on crystal precipitation allows the compound or the like represented by the above general formula (1) to be incorporated into the living body without inhibition. Therefore, the effects of co-existing components for promoting a percutaneous absorption and for promoting the absorption through the nail can be satisfactory exerted. Such effects are independent from the effects of N-methyl-2-pyrrolidone, so that the inclusion of such a component can further raise the effect of the present invention.

Further, for exerting the above-mentioned actions, the content of an α-hydroxycarboxylic acid or the like is preferably 0.1 to 20% by mass, particularly preferably 1 to 10% by mass with respect to the total amount of the pharmaceutical composition. This is because the effects may not be exerted when the content is too low, and when the content is too high, the effects reach the limit thereof and may restrict the amounts of other components to be blended.

(6) Pharmaceutical composition for external use according to the present invention In the pharmaceutical composition for external use according to the present invention, each of diester of a dibasic acid, benzyl alcohol, α-hydroxy acid, and the like exerts a combination effect with a pharmaceutical composition for external use containing the compound or the like represented by the above general formula (1) and N-methyl-2-pyrrolidone. Therefore, pharmaceutical composition for external use can be used in combination with any one of them. However, those substances promote a pharmaceutical composition for external use containing the compound or the like represented by the above general formula (1) and N-methyl-2-pyrrolidone to penetrate into the nail or the growing portion of the stratum corneum and to be retained by different mechanisms, respectively, so it is preferable to combine two or more of them, and a preferable embodiment contains at least benzyl alcohol when combined. This is because benzyl alcohol exerts an excellent inherent effect of promoting the penetration and absorption of the compound represented by the above general formula (1), which is prevented from crystal precipitation, penetration inhibition, and retention inhibition by N-methyl-2-pyrrolidone, and the combination thereof exerts a remarkable effect.

Further, it is configured more preferably in a combination of the benzyl alcohol with diester of a dibasic acid, α-hydroxy acid, or the like, most preferably in a combination of benzyl alcohol with diester of the dibasic acid and α-hydroxy acid, or the like. This is because, in addition to the effect of promoting the penetration through the nail and the growing portion of the stratum corneum and the retaining effect, temporal stability of a coating film of the composition after application of the above pharmaceutical composition for external use can be increased.

The pharmaceutical composition for external use according to the present invention can contain any of components commonly used in pharmaceutical compositions in addition to those described above, as far as, it does not impair the effects of the present invention.

Preferable examples of such components include: hydrocarbons such as vaseline and microcrystalline wax; esters such as jojoba oil and cetaceum; triglycerides such as beef tallow and olive oil; higher alcohols such as cetanol and oleyl alcohol; fatty acids such as stearic acid and oleic acid; alcohols such as ethanol and isopropanol; polyalcohols such as glycerin and 1,3-butanediol; water; non-ionic surfactants; anionic surfactants; cationic surfactants; amphoteric surfactants; thickeners such as polyvinyl pyrrolidone and carbopol; preservatives; UV absorbers; antioxidants; pigments; and powders. Those optional components and the above-mentioned essential component are treated by common procedures, whereby a pharmaceutical composition for external use of the present invention can be produced. The pharmaceutical composition for external use according to the present invention is not specifically limited as far as it is formulated into any of forms used for pharmaceutical composition for external uses, and preferable examples thereof include lotions, emulsions, gelatinizing agents, cream pharmaceuticals, aerosols, nail enamel agents, and hidrogel patches. Of those, the lotions are most preferable. For stabilizing the clarity and color of solution of the compound or the like represented by the general formula (1) or the like, 50 to 90% by mass of ethanol is most preferably contained.

The pharmaceutical composition for external use of the present invention is preferably used for treating mycotic diseases or preventing progression of the diseases by using characteristics of the compound or the like represented by the general formula (1) or the like. The mycotic diseases include: foot trichophytosis such as athlete's foot; trichophytosis corporis such as candida and pityriasis versicolor; trichophytosis on a hard keratin portion, such as onychomycosis; and trichophytosis on a hyperkeratotic portion such as heels. Because of remarkable effects, it is particularly preferable to use the pharmaceutical composition for external use of the present invention for treating the hard keratin portion, such as onychomycosis. In particular, the pharmaceutical composition for external use of the present invention exerts preferable effects on the nail and such an effect is also exerted on typical dermatomycosis. Therefore, the application of a pharmaceutical composition for external use against dermatomycosis, which satisfies the configuration of the present invention, is also within the technical scope of the present invention. Examples of such dermatomycosis include trichophytosis such as foot trichophytosis, particularly horny-outgrowing type hyperkeratotic trichophytosis which appears on heels or the like. The present invention has a significant effect on the horny-outgrowing type hyperkeratotic trichophytosis, on which the conventional agents hardly exert their effects, among the above-mentioned dermatomycosis, which is preferable.

With regard to its use, for example, the pharmaceutical composition is applied to a diseased portion one or several times a day, and the treatment is preferably carried out day after day. In particular, for onychomycosis, the compound or the like represented by the general formula (1) or the like, which is an effective component in an amount that cannot be attained by normal formulation, can be transferred into the nail. Therefore, onychomycosis or trichophytosis on a hyperkeratotic portion can be treated only by the external application without having to drink an antifungal agent over a long period of time. In addition, recurrence and reinfection have been a major problem for onychomycosis. However, the recurrence and reinfection can be prevented by application of the pharmaceutical composition for external use of the present invention for 1 to 2 weeks after abatement of the symptom. Therefore, the pharmaceutical composition for external use of the present invention exerts preventive efficacy in this aspect.

Hereinafter, the present invention will be described in more detail with reference to examples. However, the present invention is not limited to those examples.

EXAMPLES

Example 1 and Comparative Example 1

Lotion 1 containing the pharmaceutical composition of the present invention was prepared on the basis of the formulations shown in Table 1 below. That is, formulation components were dissolved by mixing at room temperature while stirring, thereby preparing each Lotion 1.

TABLE 1

| Component | % by mass |
| --- | --- |
| Lanoconazole | 1 |
| N-methyl-2-pyrrolidone | 10 |
| Benzyl alcohol | 4 |
| Diisopropyl adipate | 10 |
| Ethanol | 70.5 |
| Lactic acid | 4 |
| Polyvinyl pyrrolidone | 0.5 |
| Total | 100 |

Comparative Lotion 1 (Comparative Example 1) was prepared by replacing N-methyl-2-pyrrolidone in the formulation of Example 1 with ethanol. Lotion 1 and Comparative Lotion 1 had the clarity and color of clear and uniform. The lotions were each applied on a normal nail with a brush, and the applied surface thereof was then observed. As a result, Lotion 1 formed a smooth coating film, while Comparative Lotion 1 caused precipitation of an insolubilized product and formed an irregular coating surface. Consequently, the effect of the present invention was confirmed.

Example 2 and Comparative Example 2

According to Table 2 shown below, Lotion 2 containing the pharmaceutical composition for external use according to the present invention was prepared by the same way as that of Example 1. Comparative Lotion 2 (Comparative Example 2) was prepared by replacing N-methyl-2-pyrrolidone in the formulation of Example 2 with ethanol, followed by evaluating it by the procedures as described in Example 1. As a result, Lotion 2 formed a smooth coating film, while Comparative Lotion 2 caused the precipitation of an insolubilized product and formed an irregular coating surface.

TABLE 2

| Component | % by mass |
| --- | --- |
| Lanoconazole | 5 |
| N-methyl-2-pyrrolidone | 8 |
| Ethanol | 68.5 |
| Lactic acid | 4 |
| Benzyl alcohol | 2 |
| Diisopropyl adipate | 12 |
| Polyvinyl pyrollidone | 0.5 |
| Total | 100 |

Example 3 and Comparative Example 3

According to Table 3 shown below, Lotion 3 containing the pharmaceutical composition for external use according to the present invention was prepared by the same way as that of Example 1. Comparative Lotion 3 (Comparative Example 3) was prepared by replacing N-methyl-2-pyrrolidone in the formulation of Example 3 with ethanol.

The amounts of a agent penetrated through the nail were measured for Lotion 3 and Comparative Example 3 by a method described below. The amount of a agent penetrated through the nail (penetration absorbability ratio) for Lotion 3 was 4.5 when that of Comparative Lotion 3 was 1. Consequently, the effect of the present invention was confirmed. This is because, above mentioned, the precipitation of the insolubilized production on the applied surface is suppressed.

(Method of Measuring Amount of Agent Penetrated Through the Nail)

A topside and backside of a human nail section were sandwiched by polytetrafluoroethylene plates provided with O-shaped rings (2 mm in inner diameter) and the whole was then fixed on a Franz cell (open-top cell, Central Riken Co., Ltd.). Agar was injected into the cell on the backside of the nail and then solidified, followed by applying 0.5 µl of a sample into the O-shaped ring on the cell on the top side of the nail. The application was performed once a day for three days. After 24 hours from the last application, the nail in the O-shaped ring was punched out and luliconazole was then extracted with methanol. The extract was subjected to a high-performance liquid chromatographic method to determine the amount of luliconazole in the nail.

TABLE 3

| Component | % by mass |
| --- | --- |
| Luliconazole | 1 |
| N-methyl-2-pyrollidone | 8 |
| Ethanol | 89.5 |
| Lactic acid | 1 |
| Polyvinyl pyrollidone | 0.5 |
| Total | 100 |

INDUSTRIAL APPLICABILITY

According to the present invention, a pharmaceutical composition for external use containing a compound represented by the above general formula (1) and/or a salt thereof having an excellent penetration-absorbability can be provided.

What is claimed is:

1. An antimycotic pharmaceutical composition for external antihyperkeratotic use, comprising:
    1) luliconazole represented by a structural formula (1) below;
    2) N-methyl-2-pyrrolidone; and
    3) benzyl alcohol and/or diester of a dibasic acid, wherein the diester of the dibasic acid is a diethyl ester or a diisopropyl ester of a dibasic acid having 6-10 carbon atoms:

Structural formula (1)

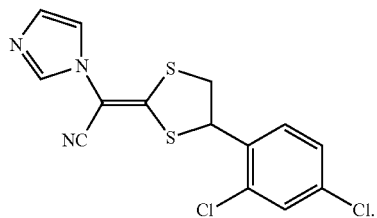

2. The antimycotic pharmaceutical composition for external antihyperkeratotic use according to claim 1, further comprising an α-hydroxycarboxylic acid and/or a salt thereof.

3. The antimycotic pharmaceutical composition for external antihyperkeratotic use according to claim 2, wherein the α-hydroxycarboxylic acid is lactic acid.

4. The antimycotic pharmaceutical composition for external antihyperkeratotic use according to claim 1, wherein the composition comprises N-methyl-2-pyrrolidone in an amount of 1 to 15% by mass of the composition.

5. The antimycotic pharmaceutical composition for external antihyperkeratotic use according to claim 1, wherein the composition comprises luliconazole in an amount of 0.5 to 15% by mass of the composition.

6. The antimycotic pharmaceutical composition for external antihyperkeratotic use according to claim 1, further comprising 50-90% by mass of ethanol.

7. The antimycotic pharmaceutical composition for external antihyperkeratotic use according to claim 1, wherein the pharmaceutical composition is a lotion.

8. A method of treating a mycotic disease comprising externally administering the composition of claim 1 to an individual in need of treatment.

9. A method according to claim 8, wherein the mycotic disease is foot trichophytosis, trichophytosis corporis, trichophytosis on a hard keratin portion, or trichophytosis on a hyperkeratotic portion.

10. A method according to claim 8, wherein the mycotic disease is onychomycosis.

11. A method according to claim 8, wherein the mycotic disease is a mycotic disease of a nail.

12. A method according to claim 8, wherein the mycotic disease is dermatomycosis.

13. The antimycotic pharmaceutical composition of claim 1 for external antihyperkeratotic use, wherein the diester of the dibasic acid is a diethyl ester or a diisopropyl ester of adipic acid or sebacic acid.

14. The antimycotic pharmaceutical composition of claim 1 for external antihyperkeratotic use, wherein the composition comprises benzyl alcohol in an amount of 1 to 15% by mass of the composition.

15. The antimycotic pharmaceutical composition of claim 1 for external antihyperkeratotic use, wherein the composition comprises the diester of the dibasic acid is a diethyl ester or a diisopropyl ester of a dibasic acid having 6-10 carbon atoms in an amount of 1 to 30% by mass of the composition.

* * * * *

UNITED STATES PATENT AND TRADEMARK OFFICE
CERTIFICATE OF CORRECTION

PATENT NO. : 8,058,303 B2
APPLICATION NO. : 12/281973
DATED : November 15, 2011
INVENTOR(S) : Miki et al.

Page 1 of 1

It is certified that error appears in the above-identified patent and that said Letters Patent is hereby corrected as shown below:

Title Page 1, Line 3 of Item (73) Assignees:, "Sinagawa-ku, Tokyo (JP)" should be changed to
--Shinagawa-ku, Tokyo (JP)--

Title Page 1, Line 4 of Item (57) Abstract, "N-methyl-2-pyrollidone;" should be changed to
--N-methyl-2-pyrrolidone;--

Title Page 2, Column 2, Line l, of Item (56) WO    WO 2007/077806    * 12/2007" should be
changed to --WO    WO   2007/077806    * 7/2007--

Column 2, Line 35, "pyrollidone, has not" should be changed to --pyrrolidone, has not--

Column 4, Line 44, "invention)" should be changed to --invention).--

Column 5, Line 23, "crystal or insolublilized" should be changed to --crystal or insolubilized--

Column 6, Line 10, "being particulary" should be changed to --being particularly--

Column 6, Line 43, "and lysin salt." should be changed to --and lysine salt.--

Column 8, Line 55, "N-methyl-2-pyrollidone" should be changed to --N-methyl-2-pyrrolidone--

Column 8, Line 59, "Polyvinyl pyrollidone" should be changed to --Polyvinyl pyrrolidone--

Column 9, Line 26, "N-methyl-2-pyrollidone" should be changed to --N-methyl-2-pyrrolidone--

Column 9, Line 30, "Polyvinyl pyrollidone" should be changed to --Polyvinyl pyrrolidone--

Column 10, Line 6, "N-methyl-2-pyrollidone" should be changed to --N-methyl-2-pyrrolidone--

Column 10, Line 8, "Polyvinyl pyrollidone" should be changed to --Polyvinyl pyrrolidone--

Signed and Sealed this
Second Day of October, 2012

David J. Kappos
*Director of the United States Patent and Trademark Office*